(12) United States Patent
Palaniappan et al.

(10) Patent No.: US 11,862,298 B1
(45) Date of Patent: Jan. 2, 2024

(54) ARTIFICIAL NEURAL NETWORK MODEL FOR PREDICTION OF MASS SPECTROMETRY DATA OF PEPTIDES OR PROTEINS

(71) Applicant: Verily Life Sciences LLC, South San Francisco, CA (US)

(72) Inventors: Krishnan Palaniappan, San Francisco, CA (US); Peter Cimermancic, Mountain View, CA (US); Roie Levy, San Francisco, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 1512 days.

(21) Appl. No.: 16/130,093

(22) Filed: Sep. 13, 2018

Related U.S. Application Data

(60) Provisional application No. 62/557,777, filed on Sep. 13, 2017.

(51) Int. Cl.
  *G16B 30/00* (2019.01)
  *G06N 3/049* (2023.01)
  (Continued)

(52) U.S. Cl.
  CPC ........... *G16B 30/00* (2019.02); *G06F 18/214* (2023.01); *G06N 3/049* (2013.01); *G16B 20/00* (2019.02);
  (Continued)

(58) Field of Classification Search
  CPC ........ G16B 30/00; G16B 40/00; G16B 40/10; G06V 10/454; G10K 2210/3038; G06N 3/049
  (Continued)

(56) References Cited

U.S. PATENT DOCUMENTS

2008/0025591 A1   1/2008   Bhanot et al.

FOREIGN PATENT DOCUMENTS

WO   2006002415   1/2006

OTHER PUBLICATIONS

T. Thireou and M. Reczko, "Bidirectional Long Short-Term Memory Networks for Predicting the Subcellular Localization of Eukaryotic Proteins," in IEEE/ACM Transactions on Computational Biology and Bioinformatics, vol. 4, No. 3, pp. 441-446, Jul.-Sep. 2007 (Year: 2007).*

(Continued)

*Primary Examiner* — G Steven Vanni
*Assistant Examiner* — Guozhen Liu
(74) *Attorney, Agent, or Firm* — Kilpatrick Townsend & Stockton LLP

(57) ABSTRACT

The present invention relates to proteomics, and techniques for predicting of mass spectrometry data of chains of amino acids, such as peptides, proteins, or combinations thereof. Particularly, aspects of the present invention are directed to a computer implemented method that includes obtaining a digital representation of a peptide sequence, the digital representation including a plurality of container elements, each container element of the plurality of container elements representing an amino acid residue; encoding, using a bidirectional recurrent neural network of long short term memory cells, each container element as an encoded vector; and decoding, using a fully-connected network, each of the encoded vectors into a theoretical output spectrum. The theoretical output spectra are represented as a one-dimensional data set or a multi-dimensional data set including intensity values for each fragment ion including one or more of the amino acid residues in the theoretical output spectra.

20 Claims, 6 Drawing Sheets

(51) Int. Cl.
  *G16B 40/00* (2019.01)
  *G16B 40/10* (2019.01)
  *G06F 18/214* (2023.01)
  *G16B 20/00* (2019.01)
  *G16B 45/00* (2019.01)
  *G16B 50/00* (2019.01)

(52) U.S. Cl.
  CPC ............ *G16B 40/00* (2019.02); *G16B 40/10* (2019.02); *G16B 45/00* (2019.02); *G16B 50/00* (2019.02)

(58) Field of Classification Search
  USPC .......................................................... 702/19
  See application file for complete search history.

(56) References Cited

OTHER PUBLICATIONS

Ngoc Hieu Tran, Xianglilan Zhang, et al and Ming Li: De novo peptide sequencing by deep learning, PNAS, Jul. 18, 2017, 114 (31) 8247-8252 (Year: 2017).*

Arnold et al., "A Machine Learning Approach to Predicting Peptide Fragmentation Spectra", Pacific Symposium on Biocomputing 11, 2006, pp. 219-230.

Bahdanau et al., "Neural Machine Translation by Jointly Learning to Align and Translate", ICLR 2015, Apr. 24, 2015, 15 pages.

Dong et al., "Prediction of Peptide Fragment Ion Mass Spectra by Data Mining Techniques", Anal. Chem., 86(15), Aug. 5, 2014, pp. 7446-7454.

Elias et al., "Intensity-based protein identification by machine learning from a library of tandem mass spectra", Nature Biotechnology, vol. 22, Jan. 18, 2004, pp. 214-219.

Käll et al., "Semi-supervised learning for peptide identification from shotgun proteomics datasets", Nature Methods vol. 4, Nov. 2007, pp. 923-925.

Kumar et al., "A mathematical programming for predicting molecular formulas in accurate mass spectrometry", IEEE International Conference on Automation Science and Engineering (CASE), Aug. 21-24, 2010, 1 page.

Zhang et al., "Current Status of Computational Approaches for Protein Identification Using Tandem Mass Spectra", Current Proteomics, vol. 4, No. 3, Oct. 1, 2007, pp. 121-130.

Zhou et al., "A machine learning approach to explore the spectra intensity pattern of peptides using tandem mass spectrometry data", BMC Bioinformatics, 9:325, Jul. 30, 2008, 17 pages.

* cited by examiner

ARTIFICIAL NEURAL NETWORK MODEL FOR PREDICTION OF MASS SPECTROMETRY DATA OF PEPTIDES OR PROTEINS

CROSS-REFERENCE TO RELATED APPLICATION

This application claims the benefit of U.S. Application No. 62/557,777, filed Sep. 13, 2017, titled "Artificial Neural Network Model For Prediction Of Mass Spectrometry Data Of Peptides Or Proteins," which is incorporated herein by reference in its entirety.

FIELD OF THE INVENTION

The present invention relates to proteomics, and in particular to techniques (e.g., systems, methods, computer program products storing code or instructions executable by one or more processors) for predicting of mass spectrometry data of chains of amino acids, such as peptides, proteins, or combinations thereof.

BACKGROUND

Mass spectrometry (MS) is a common method of chemical analysis, whereby the subject chemical species (e.g., a protein, peptide, or small molecule) is ionized and sorted based on mass-to-charge ratio (m/z) of the resultant ions. There are a variety of methods, procedures, and instrumentation (e.g., a mass analyzer) for MS used in proteomics. Typically, the MS procedure begins with ionization of a sample. Techniques for ionization include, for example, electron bombardment, fast atom bombardment, electrospray ionization, and matrix-assisted laser desorption/ionization. Ionization of a sample can result in fragmentation, whereby some of the bonds of the ionized molecules rupture to form smaller, charged fragments. All ions are then separated according to their m/z ratio. This separation typically occurs by applying an electric and/or magnetic field to the ions, causing the ions to predictably accelerate and deflect. Finally, a detector analyzes and determines the abundance of each m/z ratio in a given sample. The detector assesses the abundance by, for example, recording an induced charge or current produced when an ion passes or hits a surface of the mass analyzer. The results of the MS analysis are typically represented in a mass spectrum, which plot intensity against the m/z ratio. The x-axis of the spectrum represents the m/z ratio, and the y-axis represents ion intensity. In some spectra, the intensities can be normalized relative to the highest intensity, such that the y-axis represents relative ion abundance.

MS techniques can be used in proteomics for the analysis and identification of peptides and proteins. A common technique for protein identification by MS is known as protein fingerprinting or bottom-up proteomics. In this technique, a mixture of proteins is first digested into a collection of peptides, which is typically accomplished using an enzyme. The peptides are then subjected to tandem MS, where the m/z value of the intact peptide is first recorded (i.e., the precursor ion), then isolated, and then fragmented to create daughter (or fragment) ions. Absolute masses of the resultant ion fragments can be determined from the m/z ratio detected during MS. Peak locations within the mass spectra data provide the mass for each fragment ion, while the height of each peak represents the intensity. Each peak may correspond to a different fragment ion. The masses for the fragment ions are then compared against a library of theoretical mass spectra for known peptides. Those theoretical mass spectra are generally prepared by using computer programs according to methods known in the art. These methods include computer applications that digest a protein in silico to generate a list of theoretical peptide fragments and determining the theoretical masses of those fragments. In this way, a computer can be used to predict the theoretical masses of fragment ions that would result from the MS analysis of a given protein. While the theoretical masses can be successfully determined, there are no accurate approaches to predict the intensity of a fragment ion as would be reflected in a mass spectrum, and most MS analysis techniques rely on using a constant for intensities or no intensity information for all fragment ions. However, this strategy greatly limits the number of peptides that can be accurately identified from a given MS dataset (e.g., 50-75% of the MS features or fragment ions remain unidentified). A technique for accurately predicting the intensities of the mass spectrum of theoretical proteins and peptides would allow for more accurate identification of peptides and proteins, as well as for increasing the identification rate. Accordingly, the need exists for improved techniques for the prediction of mass spectrometry data of chains of amino acids, such as peptides, proteins, or combinations thereof.

BRIEF SUMMARY

In various embodiments, a method is provided for predicting an intensity of a fragment ion in mass spectrometry data. The method includes obtaining, by a computing device, a digital representation of a peptide sequence, the digital representation including a plurality of container elements, and each container element of the plurality of container elements representing an amino acid residue; encoding, by the computing device and using a bidirectional recurrent neural network of long short term memory cells, each container element as an encoded vector; decoding, by the computing device and using a fully-connected network, each of the encoded vectors into a theoretical output spectrum; and recording, by the computing device, the theoretical output spectrum for each of the encoded vectors as a total spectrum into a memory. The total spectrum is recorded as (i) a multi-dimensional data set of at least mass and intensity values for each fragment ion in the total spectrum, or (ii) a one-dimensional data set of intensity values for each fragment ion in the total spectrum.

In some embodiments, the container element is a one-hot vector, a set of molecular weights, or a combination thereof.

In some embodiments, the method further includes appending, by the computing device, a set of metadata features to each container element or the encoded vector for each container element. The decoding each of the encoded vectors into the theoretical output spectrum is performed based on the metadata features. Optionally, the set of metadata features include at least one of the following: ionization method, mass spectrometer type, fragmentation method, fragmentation energy, peptide charge state, peptide mass, peptide length, and peptide hydrophobicity.

In some embodiments, the encoded vector is an n-dimensional or one-dimensional vector of n elements, where n corresponds to a number of different amino acid types.

In some embodiments, the method further includes comparing, by the computing device, a multi-dimensional data set of mass and intensity values for each fragment ion in an actual mass spectra to the total spectrum. The actual mass spectra is obtained from a sample comprising a peptide sequence using mass spectrometry. The method further includes identifying, by the computing device, the peptide sequence in the sample based on the comparison.

In various embodiments, a non-transitory machine readable storage medium is provided for that has instructions stored thereon that when executed by one or more processors cause the one or more processors to perform a method including obtaining a digital representation of a peptide sequence, the digital representation including a plurality of container elements, and each container element of the plurality of container elements representing an amino acid residue; encoding, using a bidirectional recurrent neural network of long short term memory cells, each container element as an encoded vector; decoding, using a fully-connected network, each of the encoded vectors into a theoretical output spectrum; and recording the theoretical output spectrum for each of the encoded vectors as a total spectrum into a memory. The total spectrum is recorded as (i) a multi-dimensional data set of at least mass and intensity values for each fragment ion in the total spectrum, or (ii) a one-dimensional data set of intensity values for each fragment ion in the total spectrum.

In some embodiments, the container element is a one-hot vector, a set of molecular weights, or a combination thereof.

In some embodiments, the method further includes appending a set of metadata features to each container element or the encoded vector for each container element. The decoding each of the encoded vectors into the theoretical output spectrum is performed based on the metadata features. Optionally, the set of metadata features include at least one of the following: ionization method, mass spectrometer type, fragmentation method, fragmentation energy, peptide charge state, peptide mass, peptide length, and peptide hydrophobicity.

In some embodiments, the encoded vector is an n-dimensional or one-dimensional vector of n elements, where n corresponds to a number of different amino acid types.

In some embodiments, the method further includes comparing a multi-dimensional data set of mass and intensity values for each fragment ion in an actual mass spectra to the total spectrum. The actual mass spectra is obtained from a sample comprising a peptide sequence using mass spectrometry. The method further includes identifying the peptide sequence in the sample based on the comparison.

In various embodiments, a system is provided for that comprises one or more processors and non-transitory machine readable storage medium; program instructions to obtain a digital representation of a peptide sequence, the digital representation including a plurality of container elements, each container element of the plurality of container elements representing an amino acid residue; program instructions to encode, using a bidirectional recurrent neural network of long short term memory cells, each container element as an encoded vector; program instructions to decoding, using a fully-connected network, each of the encoded vectors into a theoretical output spectrum; and program instructions to record the theoretical output spectrum for each of the encoded vectors as a total spectrum into a memory. The total spectrum is recorded as (i) a multi-dimensional data set of at least mass and intensity values for each fragment ion in the total spectrum, or (ii) a one-dimensional data set of intensity values for each fragment ion in the total spectrum. The program instructions are stored on the non-transitory machine readable storage medium for execution by the one or more processor.

As used herein, the terms "various", "some", "certain", etc. embodiments or aspects may be the same embodiments or aspects, different embodiments or aspects, some embodiments or aspects that are the same, or some embodiments or aspects that are not the same.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The present invention will be better understood in view of the following non-limiting figures, in which.

DETAILED DESCRIPTION

I. Introduction

Figure 1A:
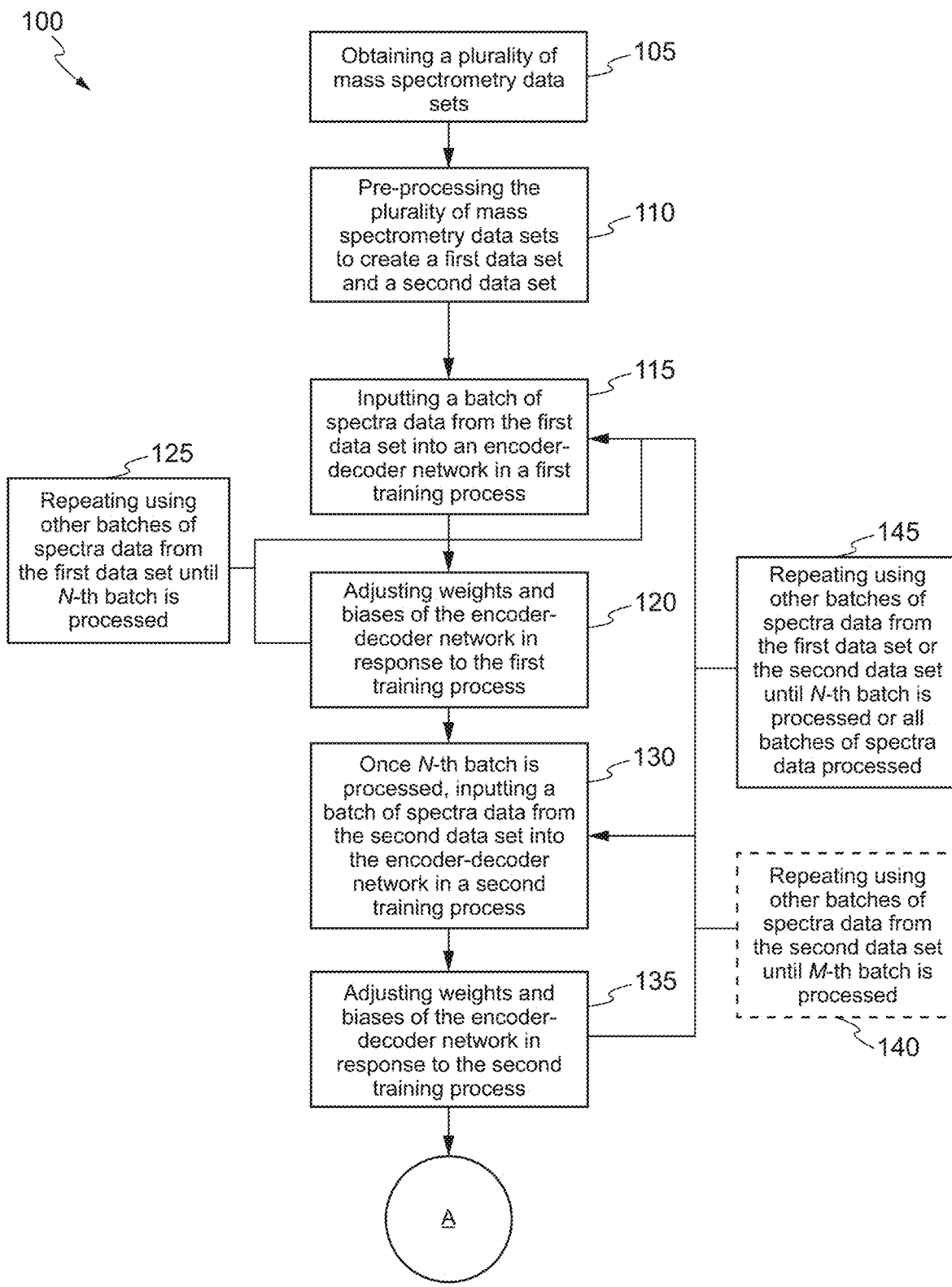
FIGS. 1A and 1B show an exemplary flow for training an encoder-decoder network for predicting an intensity of a fragment ion in mass spectrometry data in accordance with some aspects of the invention.

In various embodiments, one or more methods are provided for using a machine-learning technique to estimate one or more peak characteristics (e.g., mass and/or intensity of one or more peaks) in a mass spectrum. Each peak can be associated with a fragment ion, such that the estimated peak characteristics can be used to estimate ion-composition features of an amino-acid chain (e.g., peptide or protein). For example, an estimate can include an identity of one or more ions estimated to be present in the amino-acid chain and/or an estimated contribution of one or more ions (e.g., a number of the ions estimated to be present in the amino-acid chain). The machine-learning-based prediction results in improved accuracy and efficiency of predicting peak characteristics for a library of amino-acid chains, which can improve the accuracy and efficiency of identifying amino-acid chains in at least partly uncharacterized spectrum.

For example, the machine-learning-based predictions can be used with bottom-up strategies, in which peptide detection is used to infer protein presence. The bottom-up strategies are usually conducted in multiple workflows including "sort-then-break" and "break-then-sort." "Break-then-sort" approaches (also known as shotgun proteomics), are performed using protein digestion without any pre-fractionation/separation and the peptides are separated by liquid chromatography followed by tandem mass spectrometric analysis to obtain actual mass spectra. In a shotgun approach, the tandem actual mass spectra are collected for as many peptides as possible, and the results are then searched using an algorithmic comparison (via, for example, SEQUEST, Mascot, and Sonar) against a database of theoretical mass spectra to identify the peptides. It will be appreciated that a quality of a result of the shotgun approach thus depends on an accuracy of the theoretical spectra.

Further, the resolution and peak capacity of the liquid chromatography separation techniques are important to the success of the analysis. Multi-dimensional protein identification technology is applicable to analyses of complete cell lysates, organisms, tissue extracts, sub-cellular fractions, and other sub-proteomes.

Although the shotgun approach is conceptually simple, it results in greatly increased complexity of the generated peptide mixture, requiring highly sensitive and efficient separation of the fragments. Information is also lost upon the fragmentation of intact proteins into a mixture of peptides, which can lead to incorrect identifications. Not all peptides resulting from digestion of a protein can be observed or correctly identified with MS analysis, especially those with diverse or unexpected modifications. As used herein, "digestion" means a process whereby a protein is broken up into peptide fragments, either by chemical or enzymatic means. Furthermore, the shotgun approach relies upon a comparison of the experimentally determined MS peak mass values with predicted molecular mass values of the peptides (i.e., theoretical mass spectra) generated by a theoretical digestion of each protein in a database. As used herein, "theoretical digestion" means a process whereby a protein is digested in silico to generate a list of hypothetical peptide fragments. Consequently, the accuracy and comprehensiveness of the theoretical mass spectra is essential to the algorithmic searching and comparison performed against the database. For example, there are currently no accurate approaches to predict an intensity at a peak in the mass spectrum (representing a contribution of an ion), and the current protein fingerprinting techniques that utilize MS continue to rely on using constant intensities for all the intensities or simply no intensity data at all. Thus, the algorithmic comparison and matching between actual mass spectra and theoretical mass spectra in the shotgun approach is limited by the incomplete dataset (i.e., use of a constant for all intensities or no intensity data at all).

To address these problems, various embodiments are directed to techniques for improving the accuracy and comprehensiveness of the theoretical mass spectra, thereby improving upon the algorithmic searching and analyses performed to identify peptides and proteins within a MS dataset. For example, one illustrative embodiment of the present disclosure comprises a method for predicting an intensity at a peak in the mass spectrum (representing a contribution of an ion). In some aspects, the method comprises obtaining a digital representation of a peptide sequence, the digital representation including a plurality of container elements, each container element of the plurality of container elements representing an amino acid residue; encoding, using a bidirectional recurrent neural network of long short term memory cells, each container element as an encoded vector; and decoding, using a fully-connected network, each of the encoded vectors into a theoretical output spectrum. The theoretical output spectra are represented as a one-dimensional data set or a multi-dimensional data set including intensity values for each fragment ion including one or more of the amino acid residues in the theoretical output spectra.

Advantageously, these techniques can provide an accurate and comprehensive prediction of the theoretical mass spectra including the intensities for individual fragment ions. The improvement in the accuracy and comprehensiveness of the theoretical mass spectra, which is essential to the matching between the actual mass spectra and theoretical mass spectra, improves the capabilities of the algorithmic searching and analyses performed in shotgun proteomics. Advantageously, the improved algorithmic searching and comparison performed using theoretical mass spectra obtained in accordance with the various embodiments discussed herein, greatly increases the number of peptides that can be accurately identified from a given MS dataset (e.g., 75-95% of first stage of mass spectrometry (MS1) events are identified).

These improved theoretical mass spectra for peptides can have important applications to new areas of MS data acquisition and analysis. For example, there are computing devices that are configured to determine which peptide sequence in a database of sequences gives the best match to an unknown peptide in a sample, and the disclosed embodiments improve the functioning of these computing devices to make this determination by providing better prediction tools for fragment ion intensities. In particular, Data Independent Acquisition (DIA), spectral libraries consisting of experimentally obtained fragmentation spectrums are important to identify the peptide(s) in a given query spectrum. This is important because the query spectrum can consist of fragment ions from many different peptides and the traditional strategy of matching the fragmentation pattern with an in silico generated theoretical spectrum is insufficient due to the inability to accurately predict fragment ion intensities. However, with better prediction tools in hand, it could eliminate the need to rely on building spectral libraries for the analysis of DIA data. Consequently, a greater diversity of peptides could be identified in a given DIA experiment, including protein/peptide modifications (e.g., post-translational modifications, splice variants, cross-linking, etc.).

II. Techniques for Prediction of Mass Spectrometry Data of Peptides or Proteins FIGS. 1A, 1B, 3, and 4 depict simplified flowcharts depicting processing performed for prediction of second stage of mass spectrometry (MS2) mass spectra according to various embodiments. The steps of FIGS. 1A, 1B, 3, and 4 may be implemented in the system environments of FIGS. 2 and 5, for example. As noted herein, the flowcharts of FIGS. 1A, 1B, 3, and 4 illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combination of blocks in the block diagrams and/or flowchart illustration, can be implemented by special purpose hardware-based systems that perform the specified functions or acts, or combinations of special purpose hardware and computer instructions.

Figure 1B:
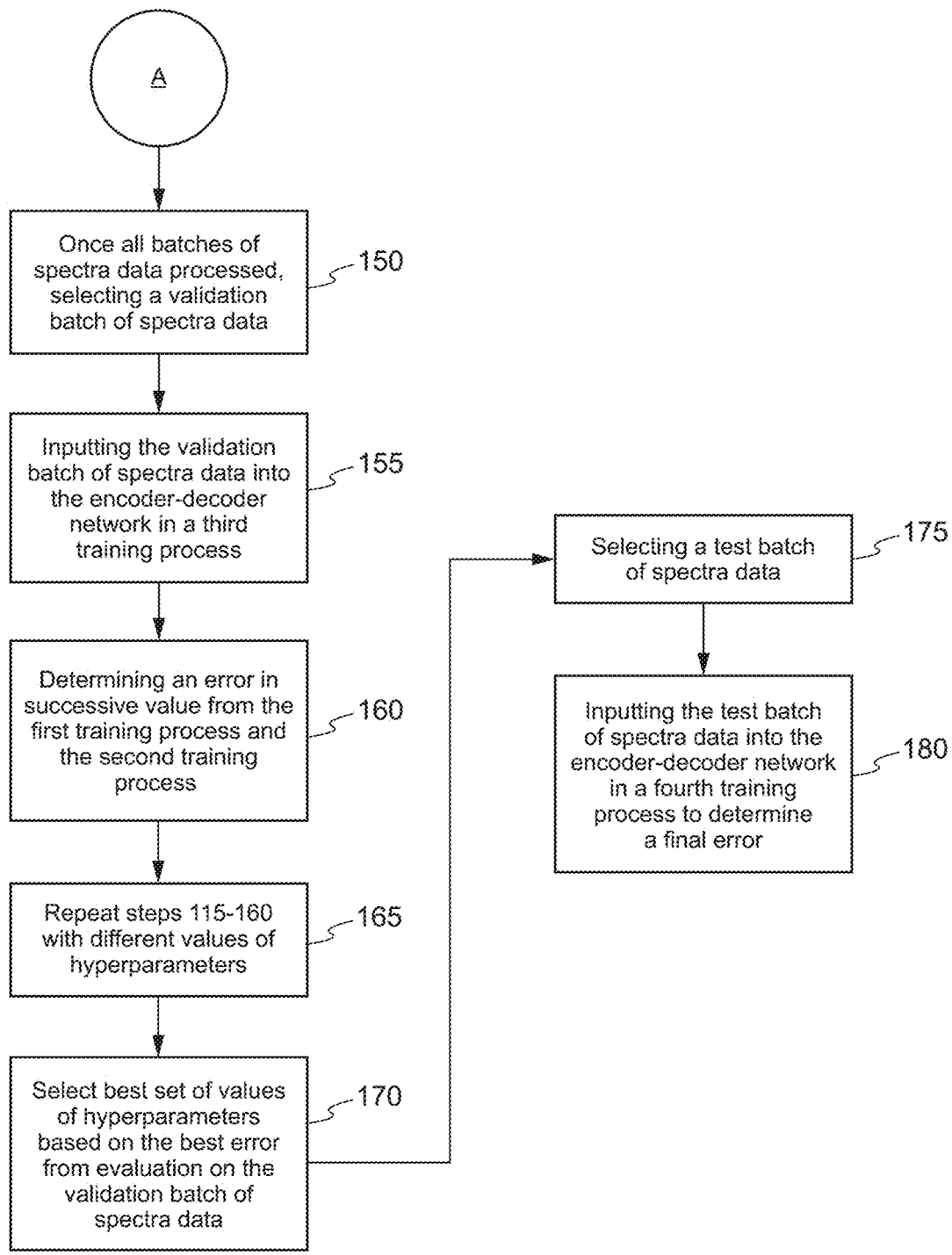

FIGS. 1A and 1B depict a simplified flowchart 100 illustrating a process for training an encoder-decoder network for predicting an intensity of a fragment ion in mass spectrometry data. With reference to FIG. 1A, at step 105, a plurality of mass spectrometry data sets may be obtained comprising peptide sequences. In some embodiments, the plurality of mass spectrometry data sets are obtained by a computing device from one or more private or public database sources, such as MassIVE Repository, PRIDE, and ProteomeXchange. The private or public database sources may be a centralized, standards compliant, data repository for proteomics data, including protein and peptide identifications, post-translational modifications and supporting spectral evidence. In certain embodiments, the plurality of mass spectrometry data sets may further include peptide or protein sequences, peptide or protein variant sequences (e.g., post-translational modifications), splice variants, isoforms, mutations, and/or enzymatic processing.

At step 110, the plurality of mass spectrometry data sets may be pre-processed to create a first data set and a second data set. As used herein, the terms "first", "second", "third" . . . "sixth", etc. identify and distinguish particular data sets, components, or processes and are not used herein to indicate a specific order of use or performance, unless otherwise stated. In various embodiments, the preprocessing includes sorting the spectra data based on accuracy of the protein or peptide identifications within the mass spectrometry data sets. As used herein, when an action is "based on" something, this means the action is based at least in part on at least a part of the something. False Discovery Rate (FDR) and Q-value may be used to assess and score the accuracy of the plurality of mass spectrometry data sets. The FDR for a set of proteins or peptides may be the expected percent of false predictions in the set of predictions. For example, if an FDR threshold of 1% is set, this means that for each data a set it is expected that 99% of the matches are correct and 1% are not correct. To describe the confidence of a specific protein or peptide identification, a Q-value may be defined as the minimal FDR required to accept the identification, after having considered all possible thresholds. However, the Q-value is an individual measurement of the false discovery rate (minimum FDR). Thus, although the Q-value is associated with a single observation, it is fundamentally a rate and hence is a property of the collection of scores $S1, \ldots, Si$. For an example: a Q-value of 0.01 for peptide ESKHTRG matching spectrum S1 means that, if we try all possible FDR thresholds, then 1% is the minimal FDR threshold at which the peptide spectrum match of the peptide to S1 will appear in the output list. The FDR and Q-values may be calculated based on spectral matching with a decoy set (peptides with shuffled or reversed sequences), as implemented in several different MS processing tools, such as MaxQuant and OpenMS.

In the some embodiments, the pre-processing is performed by the computing device and comprises: (i) identifying spectra data with unknown peptide identities, annotating the spectra data with unknown peptide identities, and adding the spectra data with unknown peptide identities having a Q-value of a predetermined number (e.g., less than 0.0001) to the first data set (e.g., "easy" cases); and (ii) identifying spectra data with known peptide identities, annotating of the spectra data with known peptide identities, and adding the spectra data with known peptide identities irrespective of their Q-value to the second data set (e.g., "difficult" cases). In certain embodiments, the identifying spectra data with unknown peptide identities includes using a spectral matching approach. For example, a spectral matching approach may include: (i) selecting a list of peptides that are expected to be identified as well as a decoy set with peptide sequences reversed, (ii) generating a theoretical MS2 spectra for true and decoy peptides, (iii) pairwise matching of all theoretical vs measured MS2 spectra, (iv) calculating a score for each comparison, and (v) fitting statistical models to scores for true and decoy peptides to calculate FDR and Q-values. In contrast to this approach for identifying spectra data with unknown peptide identities (where MS datasets are used and assumptions are made on the identity of peptides in the sample but the identity of the peptides are not known for sure), identifying spectra data with known peptide identities may include using MS datasets where the identity of the peptides going into the MS are precisely known. For example, identifying spectra data with known peptide identities may include chemically synthesizing one peptide at a time (this is in contrast to identifying spectra data with unknown peptide identities where the peptide mixture is obtained from a cell culture or tissue lysate), and inputting each peptide into the MS.

In certain embodiments, the annotating the spectra data can be performed using known software techniques, such as using MaxQuant. Thereafter, the first data set and the second data set may be divided into three subsets each, for training, validation, and testing, respectively. Accordingly, the first data set may include a first training data set, a first validation data set, and a first testing data set, while the second data set includes a second training data set, a second validation data set, and a second testing data set.

At step 115, a batch of spectra data from the first training data set may be input into an encoder-decoder network in a first training process. In the some embodiments, the inputting is performed by the computing device and the encoder-decoder network comprises a bidirectional recurrent neural network of long short term memory (LSTM) cells as the encoder portion of the network and a fully-connected neural network as the decoder portion of the network. As used herein, a "long short term memory cell" is a unit of a recurrent neural network that remembers values for either long or short time periods without using an activation function within its recurrent components. Thus, the stored value is not iteratively modified and the gradient does not tend to vanish when trained with backpropagation through time. The encoder portion maps a variable-length source sequence such as the batch of spectra data from the first training data to a fixed-dimensional vector representation, and the decoder maps the vector representation back to a variable-length target sequence such as theoretical output spectra. For example, each amino-acid residue in a peptide sequence may be represented with a one-hot vector. A single input instance (corresponding to a single peptide) is thus defined as a 2D tensor with n=<number of amino-acid residues> times <number of one-hot embeddings> dimensions. A batch of spectra data may contain multiple input instances, represented as a 3D tensor. Because peptides come in different lengths (e.g., from 5-50), the length dimension of the 3D tensor will be variable, and may need to be padded to the length of the longest peptide in any given batch. To speed up the training process, peptides of similar lengths may be bucketed together in the same batch of spectra data. The decoder may generate intensities for multiple different fragment ions (such as Y and B-ions with different charge states and with or without neutral molecule losses) for each input amino-acid residue, thus the variable lengths.

In certain embodiments, the theoretical output spectra are represented as (i) a multi-dimensional data set of mass and intensity values for each fragment ion comprising one or more of the amino acid residues in the theoretical output spectra, or (ii) a one-dimensional data set of intensity values for each fragment ion comprising one or more of the amino acid residues in the theoretical output spectra. In each data set, different intensity values represent different intensities for each fragment ion comprising the one or more of the amino acid residues within the two-dimensional data set or the one-dimensional data set (e.g., y+, y++, b+, b++, b+[-water], b++[-water], y+[-water], y++[-water], b+[-ammonium], b++[-ammonium], y+[-ammonium], y++[-ammonium]). While some embodiments are disclosed herein with respect to identifying intensity values for each fragment ion such as +, y++, b+, b++, b+[-water], b++[-water], y+[-water], y++[-water], b+[-ammonium], b++[-ammonium], y+[-ammonium], y++[-ammonium], this is not intended to be restrictive. In addition to such fragment ion types, the teachings disclosed herein can also be applied to train the encoder-decoder network to identify other types of ions such as c/z ions and other types of adducts such as +—Na, +—H, +—OH, etc.

Figure 2:
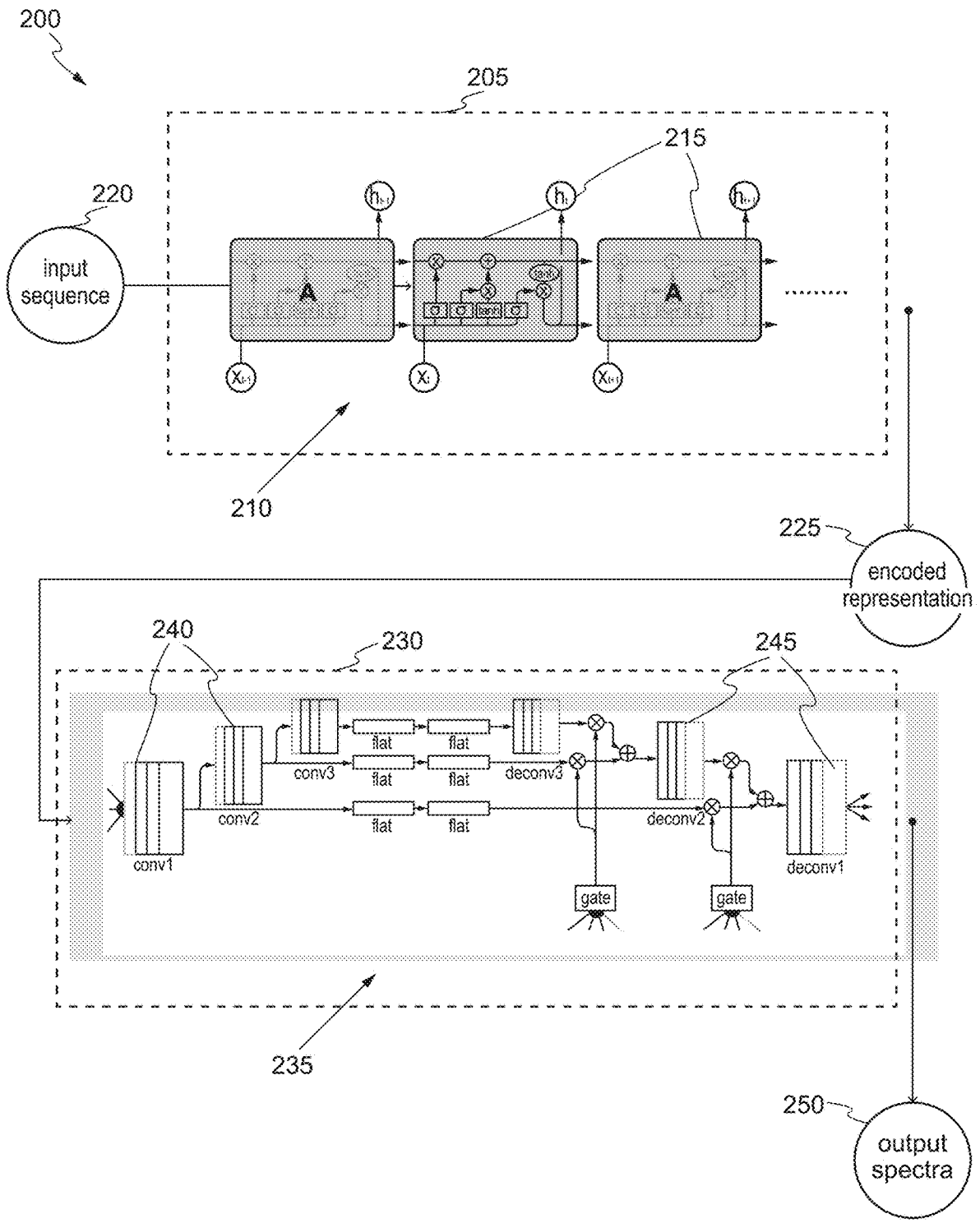
FIG. 2 shows a block diagram of an encoder-decoder network in accordance with some aspects of the invention.

As shown in FIG. 2, the encoder-decoder network 200 may comprise an encoder portion 205 including a bidirectional recurrent neural network 210 of LSTM cells 215 or an LSTM network 210. In some embodiments, the LSTM network 210 takes an input sequence 220 (a variable-length source sequence), which in step 115 is a batch of spectra data from the first training data set, and maps the input sequence 220 to an encoded representation 225 (fixed-dimensional vector representation) of the sequence. In certain embodiments, the encoded representation 225 of the input sequence 220 may be a n-dimensional vector of the batch of spectra data from the first training data set. The LSTM network 210 is configured such that each training sequence can be provided forwards and backwards to two separate recurrent neural networks (RNNs), outputs of which are concatenated and then connected to the same output layer. Unlike conventional RNNs, bidirectional RNNs utilize both the previous and future context, by processing the data from two directions with two separate hidden layers. One layer processes the input sequence in the forward direction, while the other processes the input in the reverse direction. The output of a current time step is then generated by concatenating a vector from each hidden layer. Accordingly, for every point in a given sequence, the LSTM network 210 has complete, sequential information about all points before and after it, and is capable of reading the input sequence 220, one time step at a time, to obtain the encoded representation 225. Also, because the LSTM network 210 is free to use as much or as little of this context as necessary, there is no need to find a (task-dependent) time-window or target delay size.

The encoder-decoder network 200 may further comprise a decoder portion 230 including a fully-connected neural network 235 including fully-connected layers 240 and deconvolution layers 245. The fully-connected neural network 235 is configured such that the encoded representation 225 obtained, for example, from each training sequence can be passed through the fully-connected layers 240 to get a representation of the fixed-dimensional vector representation before passing it to the deconvolution layers 245 to obtain a variable-length target sequence of theoretical output spectra 250. In some embodiments, the fully-connected network 235 takes the encoded representation 225, which in step 115 is a n-dimensional vector of the batch of spectra data from the first training data set, and maps the encoded representation 225 back to a variable-length target sequence of theoretical output spectra 250. In certain embodiments, the variable-length target sequence of theoretical output spectra 250 includes predicted values such as mass and intensity values for each fragment ion type or amino acid residue in the theoretical output spectra.

In some embodiments, the first training process may include: (i) for each input (X), performing a feed-forward pass on each intermediary layer (e.g., LSTM cells, hidden layers, fully connected layers, etc.) of the encoder-decoder network 200 to compute the outputs of each layer, then at the output layers to obtain a final output (X'); (ii) measuring a deviation between the final output (X') and the input targets (X), e.g., using a loss function such as squared root or mean-squared error, and calculating an error value for one or more nodes, cells, neurons, or layers within the encoder-decoder network; (iii) back propagating each error value back through the encoder-decoder network staring from the final output (X') until each node, cell, neuron, or layer has an associated error value which roughly represents its contribution to the final output (X'); and (iv) calculating a gradient of the loss function using the associated error values.

With reference back to FIG. 1A, at step 120, weights and biases of the encoder-decoder network may be adjusted in response to the first training process. In some embodiments, adjusting the weights and biases includes feeding the gradient of the loss function calculated in step 115 into an optimization process, which updates or adjusts the weights and biases for the one or more nodes, cells, neurons, or layers in an attempt to minimize the loss function. Accordingly, as the encoder-decoder network is trained, the nodes, cells, or neurons in the intermediate layers organize themselves in such a way that the different nodes, cells, or neurons learn to recognize different characteristics of the total input space. After training, when an arbitrary input pattern is present which contains noise or is incomplete, the nodes, cells, or neurons in the hidden layers of the network will respond with an active output if the new input contains a pattern that resembles a feature that the individual nodes, cells, or neurons have learned to recognize during their training. Optionally, the first training process may further include a pre-training process to determine initial weights and biases for the one or more nodes, cells, neurons, or layers that approximate the final solution to avoid potential problems with the backpropagation of the error values. In certain embodiments, the encoder portion and the decoder portion share weights and biases, use different sets of weights and biases, or include a combination of similar and different weights and biases.

At step 125, the inputting and the adjusting in steps 115 and 120 are repeated using other batches of spectra data from the first training data set until a predetermined number of batches of spectra data from the first training data set have been processed. In some embodiments, a discrepancy between the first data set (e.g., "easy" cases) and the second data set (e.g., "difficult" cases) is created such that the encoder-decoder network does not learn to predict only the first data set (e.g., "easy" cases). For example, a training strategy may be used in which every N-th batch or after a predetermined number of batches of spectra data from the first training data set have been processed, one or more batches of spectra data from the second training data set are used to train the encoder-decoder network. The N-th batch or the predetermined number may be a hyperparameter to be optimized in later processes.

At step 130, a batch of spectra data from the second training data set may be input into the encoder-decoder network in a second training process. In some embodiments, the second training process is similar to the first training processes, as discussed with respect to step 115. At step 135, weights and biases of the encoder-decoder network may be adjusted in response to the second training process. In some embodiments, the adjustment of the weights and biases is performed in a similar manner to the optimization process discussed with respect to step 120. Optionally, at step 140, the inputting and the adjusting in steps 130 and 135 are repeated using other batches of spectra data from the second training data set until a predetermined number of batches of spectra data from the second training data set have been processed. For example, a training strategy may be used in which every M-th batch or after a predetermined number of batches of spectra data from the second training data set have been processed, one or more batches of spectra data from the first training data set may be used again to train the encoder-decoder network. The M-th batch or the predetermined number may be a hyperparameter to be optimized in later processes.

At step 145, the inputting and the adjusting in steps (115 and 120) or (130 and 135) are repeated using other batches of spectra data from the first training data set or the second training set until (i) the predetermined number of batches of spectra data from the first training data set have been processed, or (ii) all batches of spectra data from the first training data set and the second training data set are processed, or optionally, (iii) the predetermined number of batches of spectra data from the second training data set have been processed. In some embodiments, the number of batches of spectra data may be greater than the number of data points in the sets divided by the batch size, and thus all the data points may be reused multiple times (e.g., train the model for 10-20 epochs).

With reference to FIG. 1B, at step 150, a validation batch of spectra is selected comprising spectra from the first validation data set and the second validation data set in a predetermined ratio. In some embodiments, the predetermined ratio is between 10:1 and 1:1 or between 10:1 and 5:1, for example 1:1. The preposition "between," when used to define a range of values (e.g., between x and y) means that the range includes the end points (e.g., x and y) of the given range and the values between the end points. At step 155, the selected validation batch of spectra may be input into the encoder-decoder network in a third training process. In some embodiments, the third training process is similar to the first training processes, as discussed with respect to step 115. At step 160, an error in successive value from the first training process and the second training process may be determined after all batches of spectra data from the first training data set and the second training data set are processed on the selected validation batch of spectra.

At step 165, steps 115-160 are repeated with different values for hyperparameters of the encoder-decoder network. In some embodiments, the hyperparameters include learning rate, degree of learning rate decay, batch size, number of nodes in the RNNs, number of hidden layers in the RNNs, number of layers in the fully-connected neural network, drop out probability for RNN cells, drop out probability for the fully-connected neural network layers, cell types within the RNNs, fully-connected neural network activation function, the N-th batch or the predetermined number of batches of spectra data from the first training data set, and/or optionally the M-th batch or the predetermined number of batches of spectra data from the second training data set. At step 170, the best set of values of hyperparameters is selected based on the best loss value from evaluation on the first and second validation data sets (e.g., the mean-squared error may be used as a loss function here). At step 175, a testing batch of spectra is selected comprising spectra from the first testing data set and the second testing data set in a predetermined ratio. In some embodiments, the predetermined ratio is between 1:10 and 1:1 or between 1:5 and 1:10, for example 1:1. At step 180, the selected testing batch of spectra may be input into the encoder-decoder network in a fourth training process to determine the final error of the encoder-decoder network.

Figure 3:
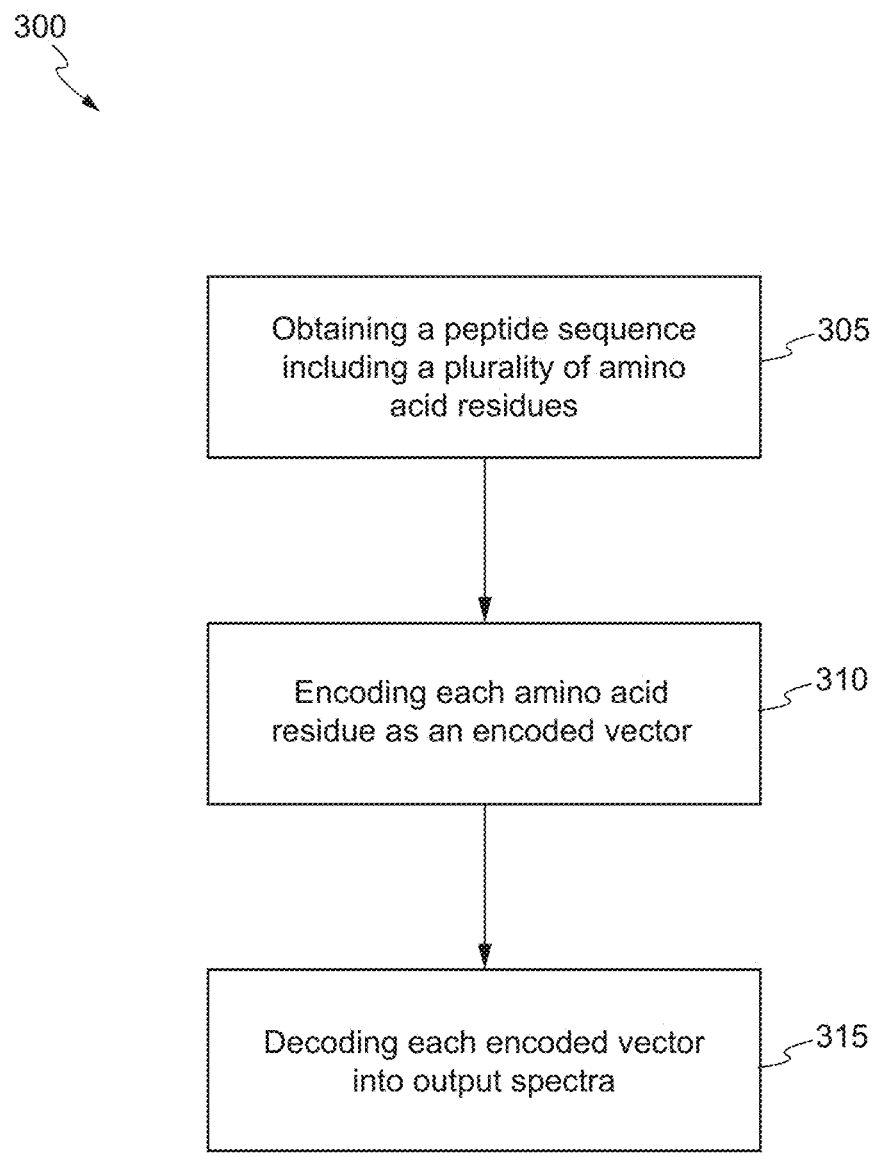
FIG. 3 shows an exemplary flow for predicting an intensity of a fragment ion in mass spectrometry data in accordance with some aspects of the invention.

FIG. 3 depicts a simplified flowchart 300 illustrating a process for predicting an intensity of a fragment ion in mass spectrometry data. At step 305, a digital representation of a peptide sequence may be obtained. In some embodiments, the digital representation includes a plurality of container elements, and each container element of the plurality of container elements represent an amino acid residue. The container element refers to an object that stores other objects (its elements) such as a one-hot vector, a set of molecular weights, or a combination thereof that uniquely identifies each amino acid residue. As used herein, the term "unique" (and any form of unique, such as "uniquely") means being substantially the only one of its kind. The term "substantially" means being largely but not necessarily wholly what is specified (and include wholly what is specified) as understood by one of ordinary skill in the art. The peptide sequence may be theoretical and obtained by a computing device from one or more private or public database sources such as MassIVE Repository, PRIDE, or ProteomXchange. The private or public database sources may be a centralized, standards compliant, data repository for proteomics data, including protein and peptide identifications, post-translational modifications and supporting spectral evidence. In certain embodiments, the plurality of amino acid residues include: (i) aliphatics such as alanine, glycine, isoleucine, leucine, proline, and valine; (ii) aromatics such as phenylalanine, tryptophan, and tyrosine; (iii) acids such as aspartic acid and glutamic acid; (iv) bases such as arginine, histidine, and lysine; (v) hydroxylic such as serine and threonine; (vi) sulphur containing such as cysteine and methionine; and/or (vii) containing an amide group such as asparagine and glutamine.

At step 310, each container element may be encoded as an encoded vector. In some embodiments, each container element is encoded, by a computing device, as an encoded vector, which is an n-dimensional or one-dimensional vector of n elements, where n corresponds to the number of different amino acid types (e.g., 20 standard amino acids plus their modifications). The encoding may be performed by an encoder including a bidirectional recurrent neural network 210 of LSTM cells as described with respect to the encoder-decoder network 200 in FIG. 2.

At step 315, each container element or the encoded vector for each container element residue may be appended with metadata. In some embodiments, the metadata includes one or more features of the peptide sequence and/or mass spectrometry techniques that could be used to identify the peptide sequence. For example, it is known that peptides of different charge or processed with different mass spec machines can result in a different spectrum. Adding such metadata features may enhance the prediction of the intensity of a fragment ion in mass spectrometry data. In certain embodiments, adding metadata improves the prediction by at least 20%. In some embodiments, the metadata is appended, by a computing device, to a data structure for either each container element or the encoded vector for each container element. In certain embodiments, the one or more features include: ionization method, mass spectrometer type (e.g., represented as a one-hot vector), fragmentation method (e.g., represented as an one-hot vector), fragmentation energy, peptide charge state (e.g., represented as a 0-1 scaled discrete value), peptide mass (e.g., represented as a 0-1 scaled continuous value), peptide length (e.g., represented as a 0-1 scaled discrete value), and/or peptide hydrophobicity (e.g., represented as a scaled continuous value). These metadata values may be scaled to the same scale as the encoded vector concatenated to the metadata values.

At step 320, each encoded vector for each amino acid residue is decoded into a theoretical output spectrum based on the set of metadata features. In some embodiments, the encoded vector is decoded, by a computing device, into the theoretical output spectrum (e.g., a n-dimensional or one-dimensional vector) that represents a corresponding amino acid residue. Thereafter, the theoretical output spectrum for each of the encoded vectors may be combined into a total spectrum for the peptide sequence The total spectrum is thus the combination of (sub)spectra from all amino acid residues of a given peptide sequence. The decoding may be performed by a decoder including a fully-connected neural network as described with respect to the encoder-decoder network 200 in FIG. 2. In certain embodiments, the total spectrum is recorded into a memory (e.g., non-transitory machine readable storage medium) such that the total spectrum can be used in subsequent processes such as part of database used to identify actual peptides or proteins within a sample. The total spectrum may be represented as (i) a multi-dimensional data set (e.g., a two-dimensional or three-dimensional data set) of at least mass and intensity values for each fragment ion in the total spectrum, or (ii) a one-dimensional data set of intensity values for each fragment ion in the total spectrum. In each data set, different intensity values may represent different intensities for each fragment ion comprising the one or more of the amino acid residues within the multi-dimensional data set or the one-dimensional data set (e.g., y+, y++, b+, b++, b+[-water], b++[-water], y+[-water], y++[-water], b+[-ammonium], b++[-ammonium], y+[-ammonium], y++[-ammonium]).

Figure 4:
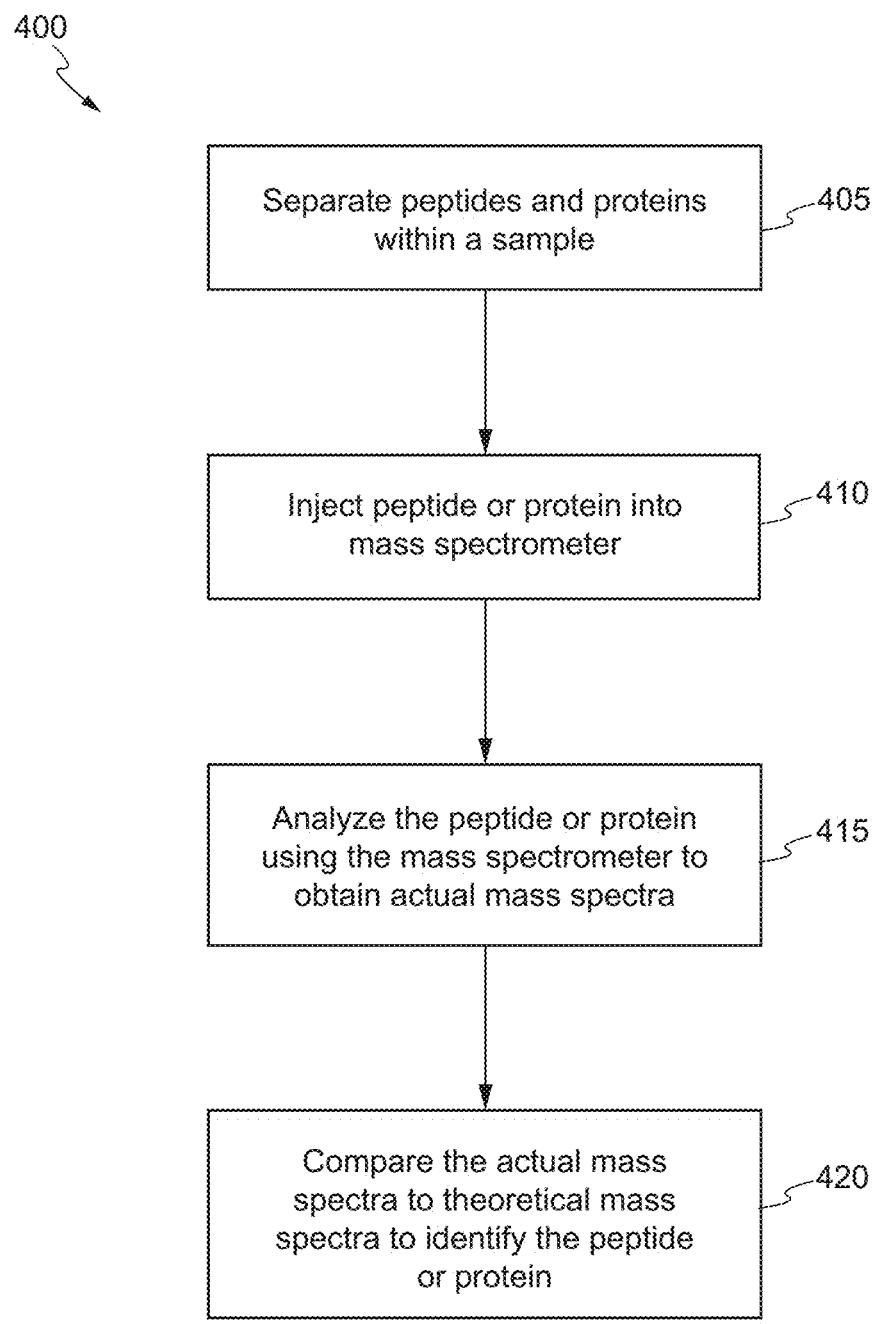
FIG. 4 shows an exemplary flow for identifying a protein or peptide in a sample in accordance with some aspects of the invention.

FIG. 4 depicts a simplified flowchart 400 illustrating a process for using theoretical output spectra obtained in accordance with aspects of the present invention to identify actual peptides or proteins within a sample. At step 405, a sample (e.g., a biological sample) is obtained, and proteins or peptides are separated. In some embodiments, the sample includes a complex mixture of proteins and molecules, which co-exist in a biological medium. The complex mixture of proteins and molecules may be separated using one or more fraction techniques. For example, the techniques of one- and two-dimensional gel electrophoresis and high performance liquid chromatography may be used for the separation of proteins or peptides. In the first technique, gel electrophoresis, the first-dimension is isoelectric focusing (IEF). In this dimension, proteins are separated by their isoelectric point (pI). The second-dimension is SDS-polyacrylamide gel electrophoresis (SDS-PAGE). In this dimension, the proteins are separated according to its molecular weight. Once the proteins are separated, in-gel digestion may occur using one or more enzymes to obtain peptides. In the second technique, high performance liquid chromatography is used to separate peptides after enzymatic digestion of the proteins. A peptide mixture that results from digestion of a protein mixture is separated by one or two dimensions of liquid chromatography.

At step 410, one or more peptides or proteins from the separated peptides or proteins is injected into a mass spectrometer and turned into an ionized form (i.e., fragmented ions) in the gas phase. In some embodiments, the one or more peptides or proteins are ionized in the gas phase using electrospray ionization (ESI) or matrix-assisted laser desorption/ionization (MALDI). In ESI, the ions are created from proteins in solution, and ESI allows fragile molecules to be ionized intact, sometimes preserving non-covalent interactions. In MALDI, the proteins are embedded within a matrix normally in a solid form, and ions are created by pulses of laser light. At step 415, the ionized form of the one or more peptides or proteins in the gas phase are accelerated in an electric or magnetic field for analysis. In various embodiments, steps 410 and/or 415 are performed using MS techniques and systems such as time-of-flight (TOF) MS, fourier transform ion cyclotron resonance (FT-ICR), or tandem mass spectrometry (MS/MS) to obtain a two-dimensional data set of mass and intensity values for each fragment ion comprising one or more of the amino acid residues in an actual mass spectra. The masses and intensities of the resultant fragment ions of the protein or peptides in the sample can be determined from the m/z ratio and abundance detected during MS, respectively.

At step 420, the one or more peptides or proteins from the sample are identified based on a comparison of the masses and intensities of the resultant fragments of the protein or peptides in the sample to theoretical mass spectrometry data within a database. In various embodiments, the two-dimensional data set of mass and intensity values for each fragment ion comprising one or more of the amino acid residues in the actual mass spectra may be compared to the theoretical mass spectrometry data in the database. The theoretical mass spectrometry data may include the masses and intensities of various peptides and proteins, as prepared in accordance with some embodiments disclosed herein (see, e.g., FIG. 3).

III. System Environment

Figure 5:
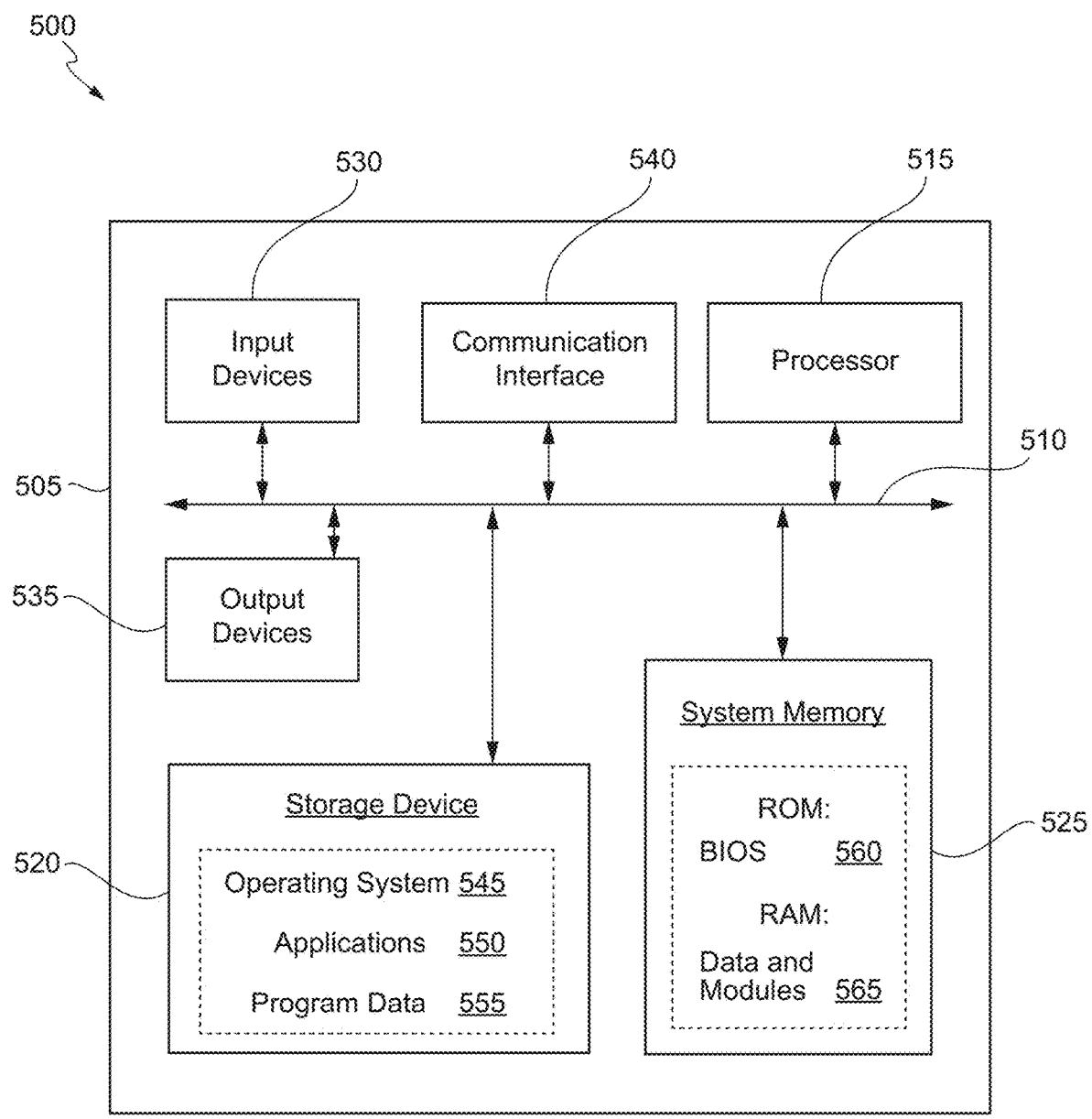
FIG. 5 shows an illustrative architecture of a computing system implemented in accordance with some aspects of the invention.

FIG. 5 is an illustrative architecture of a computing system 500 implemented as some embodiments of the present invention. The computing system 500 is only one example of a suitable computing system and is not intended to suggest any limitation as to the scope of use or functionality of the present invention. Also, computing system 500 should not be interpreted as having any dependency or requirement relating to any one or combination of components illustrated in computing system 500.

As shown in FIG. 5, computing system 500 includes a computing device 505. The computing device 605 can be resident on a network infrastructure such as within a cloud environment, or may be a separate independent computing device (e.g., a computing device of a service provider). The computing device 505 may include a bus 510, processor 515, a storage device 520, a system memory (hardware device) 525, one or more input devices 530, one or more output devices 535, and a communication interface 540.

The bus 510 permits communication among the components of computing device 505. For example, bus 510 may be any of several types of bus structures including a memory bus or memory controller, a peripheral bus, and a local bus using any of a variety of bus architectures to provide one or more wired or wireless communication links or paths for transferring data and/or power to, from, or between various other components of computing device 505.

The processor 515 may be one or more conventional processors, microprocessors, or specialized dedicated processors that include processing circuitry operative to interpret and execute computer readable program instructions, such as program instructions for controlling the operation and performance of one or more of the various other components of computing device 505 for implementing the functionality, steps, and/or performance of the present invention. In certain embodiments, processor 515 interprets and executes the processes, steps, functions, and/or operations of the present invention, which may be operatively implemented by the computer readable program instructions. For example, processor 515 can retrieve, e.g., import and/or otherwise obtain or generate a peptide sequence comprising a plurality of amino acid residues, encode each amino acid residue, append a set of metadata features to each amino acid residue or an encoded vector for each amino acid residue, and decode each encoded vector. In embodiments, the information obtained or generated by the processor 515, e.g., the peptide sequence, the plurality of amino acid residues, the encoded vectors, the decoded vectors, etc., can be stored in the storage device 520.

The storage device 520 may include removable/non-removable, volatile/non-volatile computer readable media, such as, but not limited to, non-transitory machine readable storage medium such as magnetic and/or optical recording media and their corresponding drives. The drives and their associated computer readable media provide for storage of computer readable program instructions, data structures, program modules and other data for operation of computing device 505 in accordance with the different aspects of the present invention. In embodiments, storage device 520 may store operating system 545, application programs 550, and program data 555 in accordance with aspects of the present invention.

The system memory 525 may include one or more storage mediums, including for example, non-transitory machine readable storage medium such as flash memory, permanent memory such as read-only memory ("ROM"), semi-permanent memory such as random access memory ("RAM"), any other suitable type of non-transitory storage component, or any combination thereof. In some embodiments, an input/output system 560 (BIOS) including the basic routines that help to transfer information between the various other components of computing device 505, such as during start-up, may be stored in the ROM. Additionally, data and/or program modules 565, such as at least a portion of operating system 545, program modules, application programs 550, and/or program data 555, that are accessible to and/or presently being operated on by processor 515, may be contained in the RAM. In embodiments, the program modules 565 and/or application programs 550 can comprise, for example, a processing tool to identify and annotate spectra data, a metadata tool to append data structures with metadata, an encoder-decoder network to predict theoretical mass spectrometry data, and a comparison tool to compare actual and theoretical mass spectrometry data, which provides the instructions for execution of processor 515.

The one or more input devices 530 may include one or more mechanisms that permit an operator to input information to computing device 505, such as, but not limited to, a touch pad, dial, click wheel, scroll wheel, touch screen, one or more buttons (e.g., a keyboard), mouse, game controller, track ball, microphone, camera, proximity sensor, light detector, motion sensors, biometric sensor, and combinations thereof. The one or more output devices 535 may include one or more mechanisms that output information to an operator, such as, but not limited to, audio speakers, headphones, audio line-outs, visual displays, antennas, infrared ports, tactile feedback, printers, or combinations thereof.

The communication interface 540 may include any transceiver-like mechanism (e.g., a network interface, a network adapter, a modem, or combinations thereof) that enables computing device 505 to communicate with remote devices or systems, such as a mobile device or other computing devices such as, for example, a server in a networked environment, e.g., cloud environment. For example, computing device 505 may be connected to remote devices or systems via one or more local area networks (LAN) and/or one or more wide area networks (WAN) using communication interface 540.

As discussed herein, computing system 500 may be configured to train an encoder-decoder network to predict theoretical mass spectrometry data, predict the theoretical mass spectrometry data, and compare actual mass spectrometry data to the theoretical mass spectrometry data to identify one or more proteins or peptides in a sample. In particular, computing device 505 may perform tasks (e.g., process, steps, methods and/or functionality) in response to processor 515 executing program instructions contained in non-transitory machine readable storage medium, such as system memory 525. The program instructions may be read into system memory 525 from another computer readable medium (e.g., non-transitory machine readable storage medium), such as data storage device 520, or from another device via the communication interface 540 or server within or outside of a cloud environment. In embodiments, an operator may interact with computing device 505 via the one or more input devices 530 and/or the one or more output devices 535 to facilitate performance of the tasks and/or realize the end results of such tasks in accordance with aspects of the present invention. In additional or alternative embodiments, hardwired circuitry may be used in place of or in combination with the program instructions to implement the tasks, e.g., steps, methods and/or functionality, consistent with the different aspects of the present invention. Thus, the steps, methods and/or functionality disclosed herein can be implemented in any combination of hardware circuitry and software.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A method for predicting an intensity of a fragment ion in mass spectrometry data, the method comprising:
    obtaining, by a computing device, a digital representation of a peptide sequence, the digital representation including a plurality of container elements, and each container element of the plurality of container elements representing an amino acid residue;
    encoding, by the computing device and using a bidirectional recurrent neural network of long short term memory cells, each container element as an encoded vector;
    decoding, by the computing device and using a fully-connected network, each of the encoded vectors into a theoretical output spectrum; and
    recording, by the computing device, the theoretical output spectrum for each of the encoded vectors as a total spectrum into a memory,
    wherein the total spectrum is recorded as (i) a multi-dimensional data set of at least mass and intensity values for each fragment ion in the total spectrum, or (ii) a one-dimensional data set of intensity values for each fragment ion in the total spectrum.

2. The method of claim 1, wherein the container element is a one-hot vector, a set of molecular weights, or a combination thereof.

3. The method of claim 1, further comprising appending, by the computing device, a set of metadata features to each container element or the encoded vector for each container element, wherein the decoding each of the encoded vectors into the theoretical output spectrum is performed based on the metadata features.

4. The method of claim 3, wherein the set of metadata features include at least one of the following: ionization method, mass spectrometer type, fragmentation method, fragmentation energy, peptide charge state, peptide mass, peptide length, and peptide hydrophobicity.

5. The method of claim 1, wherein the encoded vector is an n-dimensional or one-dimensional vector of n elements, where n corresponds to a number of different amino acid types.

6. The method of claim 1, further comprising:
comparing, by the computing device, a multi-dimensional data set of mass and intensity values for each fragment ion in an actual mass spectra to the total spectrum, wherein the actual mass spectra is obtained from a sample comprising a peptide sequence using mass spectrometry; and
identifying, by the computing device, the peptide sequence in the sample based on the comparison.

7. A non-transitory machine readable storage medium having instructions stored thereon that when executed by one or more processors cause the one or more processors to perform a method comprising:
obtaining a digital representation of a peptide sequence, the digital representation including a plurality of container elements, each container element of the plurality of container elements representing an amino acid residue;
encoding, using a bidirectional recurrent neural network of long short term memory cells, each container element as an encoded vector;
decoding, using a fully-connected network, each of the encoded vectors into a theoretical output spectrum; and
recording the theoretical output spectrum for each of the encoded vectors as a total spectrum into a memory,
wherein the total spectrum is recorded as (i) a multi-dimensional data set of at least mass and intensity values for each fragment ion in the total spectrum, or (ii) a one-dimensional data set of intensity values for each fragment ion in the total spectrum.

8. The non-transitory machine readable storage medium of claim 7, wherein the container element is a one-hot vector, a set of molecular weights, or a combination thereof.

9. The non-transitory machine readable storage medium of claim 7, wherein the method further comprises appending a set of metadata features to each container element or the encoded vector for each container element, wherein the decoding each of the encoded vectors into the theoretical output spectrum is performed based on the metadata features.

10. The non-transitory machine readable storage medium of claim 9, wherein the set of metadata features include at least one of the following: ionization method, mass spectrometer type, fragmentation method, fragmentation energy, peptide charge state, peptide mass, peptide length, and peptide hydrophobicity.

11. The non-transitory machine readable storage medium of claim 7, wherein the encoded vector is an n-dimensional or one-dimensional vector of n elements, where n corresponds to a number of different amino acid types.

12. The non-transitory machine readable storage medium of claim 7, wherein the method further comprises:
comparing a multi-dimensional data set of mass and intensity values for each fragment ion in an actual mass spectra to the theoretical output spectra, wherein the actual mass spectra is obtained from a sample comprising a peptide sequence using mass spectrometry; and
identifying the peptide sequence in the sample based on the comparison.

13. A system comprising:
one or more processors and non-transitory machine readable storage medium;
program instructions to obtain a digital representation of a peptide sequence, the digital representation including a plurality of container elements, each container element of the plurality of container elements representing an amino acid residue;
program instructions to encode, using a bidirectional recurrent neural network of long short term memory cells, each container element as an encoded vector;
program instructions to decoding, using a fully-connected network, each of the encoded vectors into a theoretical output spectrum; and
program instructions to record the theoretical output spectrum for each of the encoded vectors as a total spectrum into a memory,
wherein the total spectrum is recorded as (i) a multi-dimensional data set of at least mass and intensity values for each fragment ion in the total spectrum, or (ii) a one-dimensional data set of intensity values for each fragment ion in the total spectrum, and
wherein the program instructions are stored on the non-transitory machine readable storage medium for execution by the one or more processors.

14. The system of claim 13, wherein the container element is a one-hot vector, a set of molecular weights, or a combination thereof.

15. The system of claim 13, further comprising program instructions to append a set of metadata features to each container element or the encoded vector for each container element, wherein the decoding each of the encoded vectors into the theoretical output spectrum is performed based on the metadata features.

16. The system of claim 15, wherein the set of metadata features include at least one of the following: ionization method, mass spectrometer type, fragmentation method, fragmentation energy, peptide charge state, peptide mass, peptide length, and peptide hydrophobicity.

17. The system of claim 13, wherein the encoded vector is an n-dimensional or one-dimensional vector of n elements, where n corresponds to a number of different amino acid types.

18. The system of claim 13, further comprising:
program instructions to compare a multi-dimensional data set of mass and intensity values for each fragment ion in an actual mass spectra to the theoretical output spectra, wherein the actual mass spectra is obtained from a sample comprising a peptide sequence using mass spectrometry; and
program instructions to identify the peptide sequence in the sample based on the comparison.

19. A method of training an encoder-decoder network for predicting an intensity of a fragment ion in mass spectrometry data, the method comprising:
 obtaining, by a computing device, a plurality of mass spectrometry data sets comprising peptide sequences;
 pre-processing, by the computing device, the plurality of mass spectrometry data sets to create a first data set and a second data set, wherein the pre-processing comprises (i) identifying spectra data with unknown peptide identities, annotating the spectra data with unknown peptide identities, and adding the spectra data with unknown peptide identities having a Q-value of a predetermined number to the first data set; and (ii) identifying spectra data with known peptide identities, annotating the spectra data with known peptide identities, and adding the spectra data with known peptide identities irrespective of their Q-value to the second data set;
 inputting, by the computing device, a batch of spectra data from the first data set into the encoder-decoder network in a first training process;
 adjusting, by the computing device, weights and biases of the encoder-decoder network in response to the first training process;
 repeating, by the computing device, the inputting and the adjusting using other batches of spectra data from the first data set until a predetermined number of batches of spectra data from the first data set have been processed;
 inputting, by the computing device, a batch of spectra data from the second data set into the encoder-decoder network in a second training process;
 adjusting, by the computing device, weights and biases of the encoder-decoder network in response to the second training process;
 repeating, by the computing device, the inputting and the adjusting using other batches of spectra data from the first data set until (i) the predetermined number of batches of spectra data from the first data set have been processed, or (ii) all batches of spectra data from the first data set and the second data set are processed;
 determining, by the computing device, an error in successive values from the first training process and the second training process after all batches of spectra data from the first data set and the second data set are processed;
 selecting, by the computing device, a validation batch of spectra data comprising spectra data from the first data set and the second data set in a 1:1 ratio;
 inputting, by the computing device, the validation batch of spectra data into the encoder-decoder network in a third training process;
 determining, by the computing device, an error in successive values from the first training process and the second training process after all batches of spectra data from the first training data set and the training second data set are processed;
 repeating, by the computing device, the first training process, the second training process, and the third training process with different values for one or more hyperparameters;
 selecting, by the computing device, an optimal set of values of the one or more hyperparameters based on error from evaluation on the first training process, the second training process, and the third training process;
 selecting, by the computing device, a testing batch of spectra data comprising spectra data from the first data set and the second data set in a 1:1 ratio;
 inputting, by the computing device, the testing batch of spectra data into the encoder-decoder network in a fourth training process; and
 determining, by the computing device, an error on the fourth training process.

20. The method of claim 19, wherein the one or more hyperparameters include at least one of the following hyperparameters: learning rate, degree of learning rate decay, batch size, number of hidden nodes in a recurrent neural network, number of hidden layers in the recurrent neural network, number of layers in a fully-connected neural network, drop out probability for the recurrent neural network cells, drop out probability for the fully-connected neural network layers, cell types within the recurrent neural network, fully-connected neural network activation function, and the predetermined number of batches of spectra data from the first data set.

* * * * *